(12) United States Patent
Zelechonok

(10) Patent No.: US 9,950,278 B1
(45) Date of Patent: Apr. 24, 2018

(54) CHROMATOGRAPHY COLUMN WITH INLET AND OUTLET AT ONE END

(71) Applicant: Yury Zelechonok, Northbrook, IL (US)

(72) Inventor: Yury Zelechonok, Northbrook, IL (US)

( * ) Notice: Subject to any disclaimer, the term of this patent is extended or adjusted under 35 U.S.C. 154(b) by 211 days.

(21) Appl. No.: 15/089,436

(22) Filed: Apr. 1, 2016

Related U.S. Application Data

(60) Provisional application No. 62/142,582, filed on Apr. 3, 2015.

(51) Int. Cl.
*B01D 15/14* (2006.01)
*B01D 15/22* (2006.01)

(52) U.S. Cl.
CPC .............. *B01D 15/14* (2013.01); *B01D 15/22* (2013.01)

(58) Field of Classification Search
CPC .................................. B01D 15/14; B01D 15/22
See application file for complete search history.

(56) References Cited

U.S. PATENT DOCUMENTS

| 4,876,005 | A | 10/1989 | America |
| 4,968,421 | A | 11/1990 | Spacek et al. |
| 5,651,885 | A | 7/1997 | Schick |
| 5,736,036 | A | 4/1998 | Upchurch et al. |
| 7,125,489 | B2 | 10/2006 | Zelechonok et al. |
| 7,901,573 | B2 | 3/2011 | Ishii et al. |
| 7,937,990 | B2 | 5/2011 | Nagaoka et al. |
| 8,544,350 | B2 | 10/2013 | Itafuji et al. |
| 2008/0017580 | A1* | 1/2008 | Gebauer ................ B01D 15/22 210/656 |
| 2009/0321338 | A1* | 12/2009 | Natarajan .......... B01D 15/1864 210/198.3 |
| 2012/0325052 | A1* | 12/2012 | Rosch .................... B01D 15/22 75/393 |
| 2013/0062267 | A1* | 3/2013 | Gebauer .............. B01D 15/206 210/198.2 |
| 2013/0193052 | A1* | 8/2013 | Witt ...................... B01D 15/206 210/198.2 |
| 2013/0270167 | A1* | 10/2013 | Raedts ................... B01D 15/22 210/198.2 |
| 2016/0067634 | A1* | 3/2016 | Richardson ........... B01D 15/22 210/488 |

\* cited by examiner

*Primary Examiner* — Chester T Barry
(74) *Attorney, Agent, or Firm* — John C. Shepard

(57) ABSTRACT

A chromatography column includes a shell containing packed stationary phase and includes an inlet and an outlet at one end of the shell. A plastic sleeve is positioned in the shell to isolate the stationary phase from the shell. A capillary tube extends from an upstream inlet at the one end of the shell to deliver mobile phase to the upstream end of the stationary phase. Mobile phase travels through the stationary phase and exits the column at the one end. Porous filters and seals are provided. A removable coupling adapter is attached to the one end of the column and provides short flow paths and connection ports for the column inlet and outlet. The coupling adapter may incorporate other chromatography components, such as temperature control elements or flow cell optical detectors.

21 Claims, 6 Drawing Sheets

US 9,950,278 B1

CHROMATOGRAPHY COLUMN WITH INLET AND OUTLET AT ONE END

CROSS-REFERENCE TO RELATED APPLICATIONS

This application claims the benefit of Provisional Patent Application Ser. No. 62/142,582, filed Apr. 3, 2015.

BACKGROUND OF THE INVENTION

Technical Field

The present invention relates to a chromatography column and, more particularly, to a chromatography column in which the inlet and outlet are located on the same end of the column and to which a coupling adapter is attached.

Background Art

High pressure liquid chromatography (HPLC) systems include chromatography columns and often various other fluidic devices or components, including, but not limit to pumps, valves, guard columns, detectors, couplings, and the like, which are connected together by capillary tubes providing fluid communication. These HPLC systems operate at pressures of 5,000 PSI and higher. In ultra high pressure liquid chromatography (UHPLC), which is increasingly being used today, fluid pressures may be substantially higher, often exceeding 15,000 PSI. To withstand these pressures, capillary tubes that connect the various system components are formed from an advanced polymer or plastic or stainless steel. End fittings or couplings are used to tightly clamp, seal and connect the tubes to the chromatography components.

Typically, chromatography columns are made from thick internally polished stainless steel tubes with fluid flowing from one end directly to the other end. Polished stainless steel tubes are relatively expensive. In addition, straight-through columns require longer lengths of tubing to interconnect the various chromatography components. Stainless steel conducts heat poorly when a column needs to be thermally controlled.

In addition, conventional columns often require fittings or wrenches to connect high pressure capillaries. If a column leaks due to a poor connection or overpressure, the liquid mobile phase can create a spill, so a special leak detector needs to be used that warns the user about leakage.

BRIEF SUMMARY OF THE INVENTION

The present invention is directed to overcoming one or more of the problems as set forth above.

The primary object of the present invention is to provide a chromatography column having its inlet and outlet at one end.

It is a further object of the present invention to provide a chromatography column that uses less stainless steel and employs less expensive metals and plastics.

It is an additional object of the present invention to provide a chromatography column that requires fewer connecting tubes.

It is another object of the present invention to provide a chromatography column wherein the external flow paths for the mobile phase are relatively short.

It is another object of present invention to provide a chromatography column that does not spill the mobile phase even when a high pressure connection has failed.

It is another object of present invention to provide a chromatography column that is easy to install.

It is another object of the present invention to provide a chromatography column that may be attached to a coupling adapter having conventional chromatographic inlet and outlet ports so the column can be utilized in conventional chromatography systems.

It is still another object of the present invention to provide a coupling adapter internally incorporating other chromatography system components.

It is still another object of this invention to provide a coupling adapter incorporating temperature controls, flow cell optical detectors, and the like.

In an exemplary embodiment of the present invention, a chromatography column includes an outer shell having an internal sleeve containing packed stationary phase and a capillary tube with an inlet located at one end of the shell delivering mobile phase to the stationary phase, the mobile phase then exiting from an outlet located at the same shell end.

In one aspect of the present invention, the shell includes a sleeve lining the shell's internal surface that is formed from a chemically inert or non-reactive plastic.

In another aspect of the present invention, the shell is made of a metal that is not stainless steel, such as aluminum.

In another aspect of the present invention, the column is closed at one end by a coupling adapter defining conventional inlet and outlet ports enabling connection to various other chromatography components and the other column end is closed by a removable end cap.

A further feature of the present invention is that a temperature control element is built into the coupling adapter enabling the temperature of the chromatographic components and the fluid therein to be maintained or adjusted hotter or colder.

In another aspect of the present invention, flow paths are defined internally within the coupling adapter thereby eliminating lengths of connecting tubing that would otherwise dissipate heat or cold or would broaden peaks in resulting chromatograms and reduce efficiency.

In yet another aspect of the present invention, one of the internal flow paths extends between two spaced windows to define a flow cell optical path. By using internal flow paths, any column leaks are internally contained, unlike conventional column systems where leaks are external and uncontained.

BRIEF DESCRIPTION OF THE SEVERAL VIEWS OF THE DRAWINGS

The details of construction and operation of the invention are more fully described with reference to the accompanying drawings which form a part hereof and in which like reference numerals refer to like parts throughout.

In the drawings.

Figure 1:
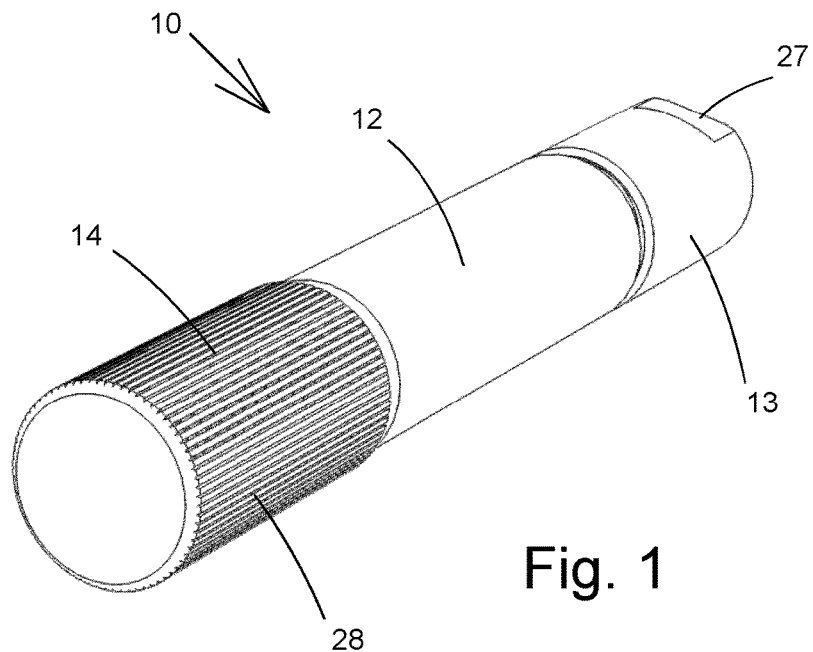
FIG. 1 is an external perspective view of an embodiment of a chromatography column with a protective end cap attached employing the principles of the invention.
Figure 2:
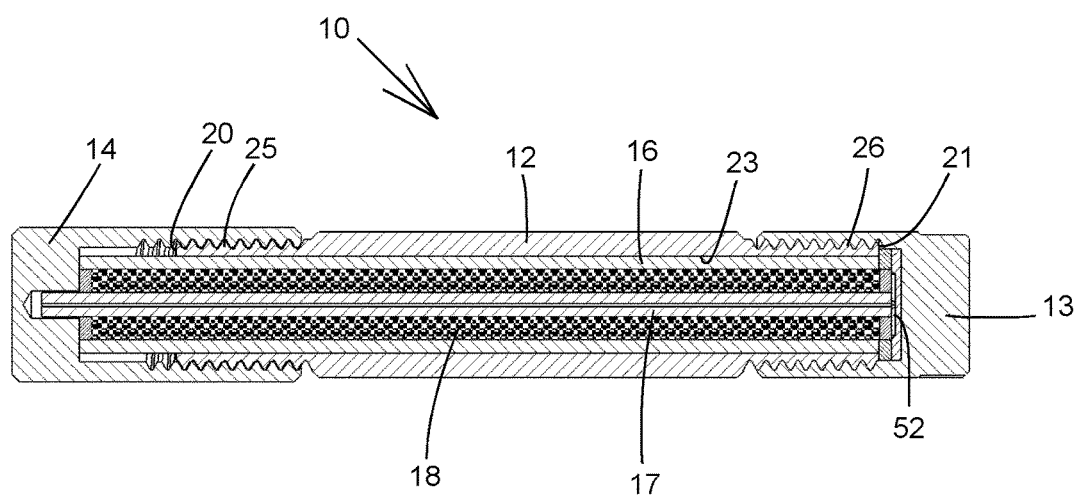
FIG. 2 is a cross-sectional view of the chromatography column shown in FIG. 1.
Figure 3:
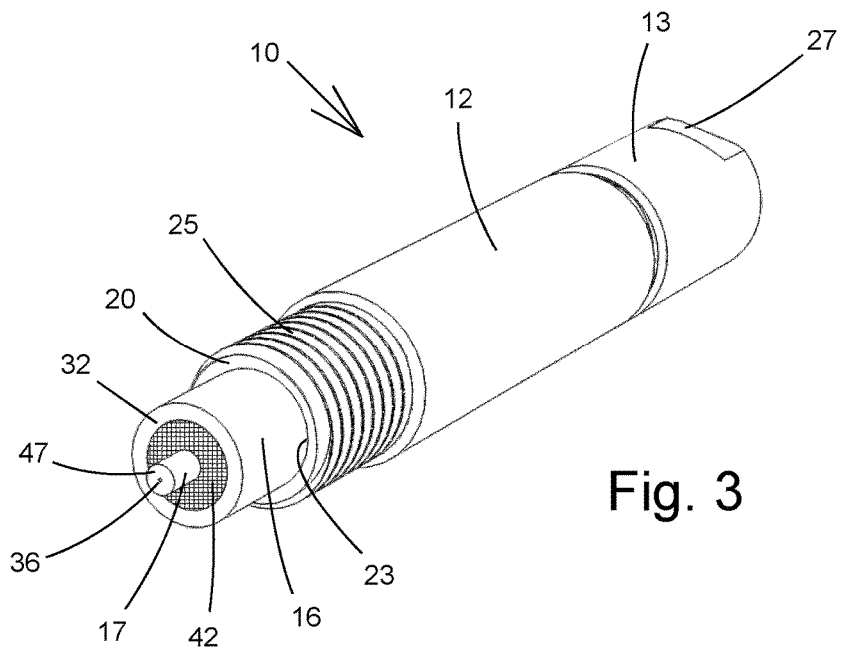
FIG. 3 is an external perspective view of the chromatography column shown in FIG. 1 without the protective end cap.
Figure 4:
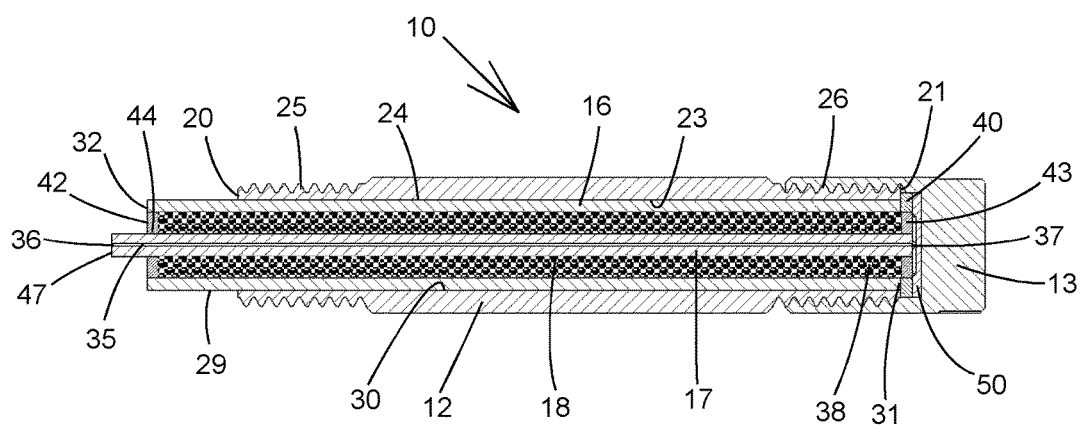
FIG. 4 is a cross-sectional view of the chromatography column shown in FIG. 3.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood.

DETAILED DESCRIPTION OF THE PREFERRED EMBODIMENTS

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

This invention generally relates to high pressure liquid chromatography ("HPLC") and to ultra high pressure liquid chromatography ("UHPLC"), but is not limited thereto and may be employed in other fields as well. An HPLC system may include a chromatography column and various fluidic devices or components, including, but not limit to a pump, valve, guard column, detector, couplings, and the like, which are connected together by capillary tubes providing fluid communication.

In FIGS. 1-6, a liquid chromatography column, generally designated 10, is seen to externally include an outer shell 12, an end cap 13 on the distal end of the shell, and a temporary protective end cap 14 on the proximal end of the shell. Internally, the liquid chromatography column includes an internal sleeve 16, a capillary tube 17, and packed particulate chromatography material 18. The column 10 may be made to any desired length, but it is contemplated that the column 10 will typically have a length between 10 millimeters and 250 millimeters.

The elongate shell 12, or housing, extends along a longitudinal axis between proximal and distal ends 20 and 21, respectively, and has a cylindrical through bore 23 with an internal surface 30 defining an interior space 24. External threads 25 and 26 are provided adjacent each end 20 and 21 that are adapted to be threaded into end caps 13 and 14 or into an adapter coupling described thereafter. To facilitate turning of the end caps, the distal end cap 13 has opposed flats 27 for tool gripping, while the proximal end cap 14 has external grooves or ridges 28 for manual gripping. The proximal end cap 14 is temporary and guards the capillary tube 17 and column material 18 from damage and contamination during transport and storage and is removed prior to use. The shell 12 and end caps 13 and 14 can be made from any metal including stainless steel, but as contemplated herein can be inexpensively and easily produced from aluminum or plastic.

The cylindrical tubular sleeve 16 is coaxial and concentric with the outer shell 12 and has an external surface 29 adjoining the shell internal surface 30. The sleeve 16 has a distal end 31 aligned with the shell distal end 21, a proximal end 32 extending axially outward from the shell proximal end 20, and defines an interior space 33. The sleeve 16 is of a size and configuration to fit snugly within the shell 12. The tubular sleeve 16 can be made from plastic, particularly from plastic materials that are generally non-reactive or chemically inert, including polyethylene, or from polytetrafluoroethylene ("Teflon®").

The capillary tube 17 is coaxial with the sleeve 16 and extends longitudinally along the column axis. The capillary tube 17 defines a capillary passage 35 through which chromatographic fluid, the mobile phase, is moved from a proximal upstream inlet 36 out of the downstream distal outlet 37 to the high pressure upstream distal end 38 of the packed chromatographic material, the stationary phase. The capillary tube 17 and the sleeve 16 define a space therebetween into which the packed column material is disposed. When the column is packed with chromatographic material, such as silicagel, at pressures of 5000 PSI or more, the silicagel becomes pressed into the relatively soft plastic of the capillary tube 17 holding it firmly in place. The capillary tube 17 is made from polyetheretherketone ("PEEK"), or a similar high performance plastic or metal.

An annular sealing gasket 40 of suitable relatively soft compressible material is disposed at the distal end 21 of the shell 12 so that when the end cap 13 is threaded on the shell 12 a seal is made between the end cap 13, the shell 12 and the sleeve 16.

End elements comprising porous sintered metal filters 42 and 43, or frits, are located at the upstream and downstream ends of the column material space 33 to hold the column material 18 in place. A small central opening 44 is defined in each filter 42 and 43 permitting the capillary tube 17 to extend therethrough and be held snugly therein. The capillary tube 17 extends axially outward from the sleeve proximal end 32 and axially outward from the sleeve distal end 31 to deliver fluid to the upstream side of the upstream filter 43.

Figure 5:
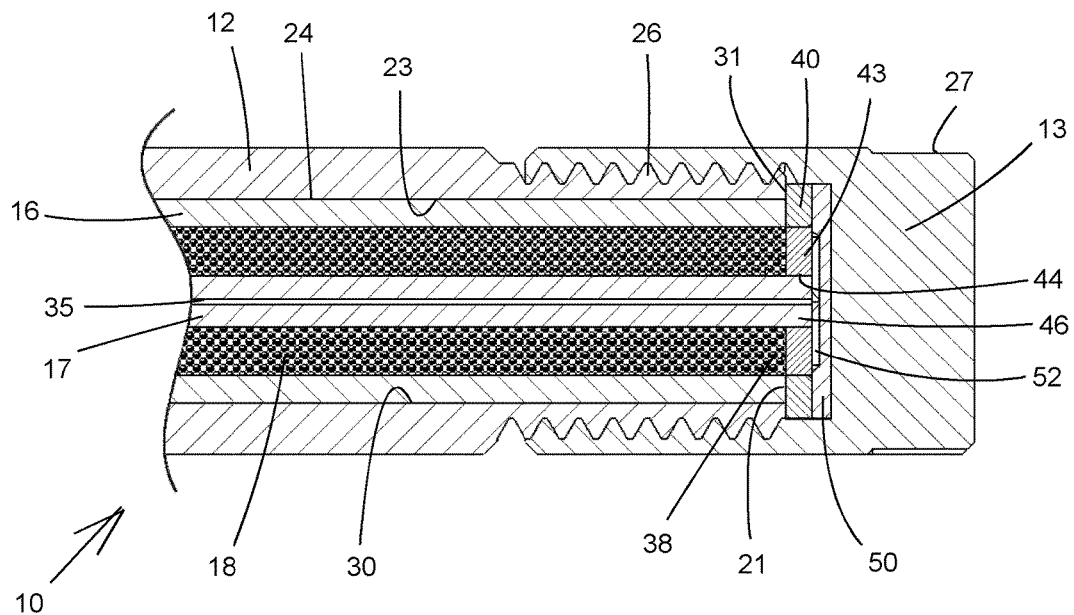
FIG. 5 is an enlarged cross-sectional view of the distal end of the chromatography column shown in FIG. 3.
Figure 6:
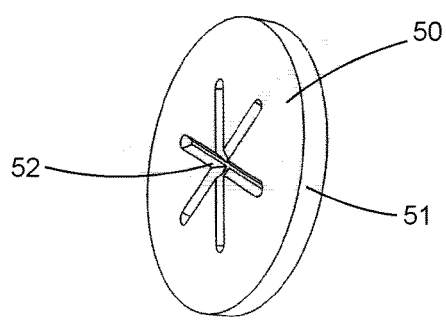
FIG. 6 is an enlarged perspective view of an embodiment of a spreader disk employed in the chromatography column.

As best seen in FIG. 5, the distal end 46 of the capillary tube 17 is held in isolated position spaced from the end cap 13 such that fluid from the capillary tube 17 flows through a flow path through the filter and downstream into the column material 18. A liquid spreader 50 is disposed in the end space 55 between the downstream end 46 of the capillary tube 17 and the end cap 13 and, as best seen in FIG. 6, comprises a disk 51 with radial extending grooves 52, or flow paths, to distribute mobile phase fluid across the outboard surface of the upstream distal filter 43. Other means can be used to deliver fluid from the capillary tube 17 to the filter 43, including eliminating the spreader disk and inserting a spacer or forming a concavity in the internal surface of the end cap.

Fluid flowing from the downstream end of the column material 18 passes through the end filter 42 and exits the column 10. The sleeve end 32 forms the fluid outlet that is radially outward from the axially located capillary tube inlet 36, both of which are located at the proximal end of the column 10.

Figure 7:
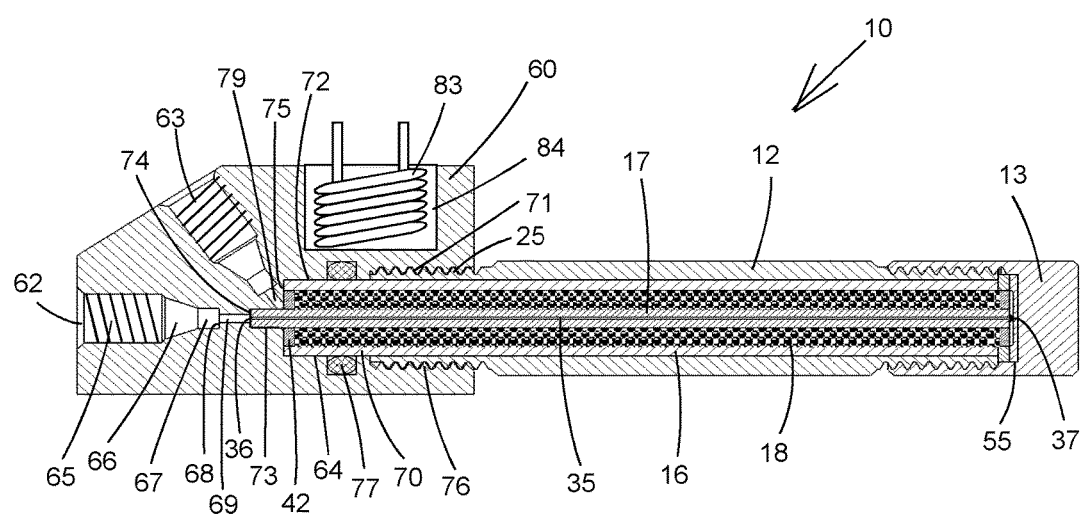
FIG. 7 is a cross-sectional view of the chromatography column shown in FIG. 4 attached to an adapter having inlet and outlet ports and a built-in temperature control.

In FIG. 7, a coupling adapter 60 that is formed from an integral block of metal, such as stainless steel, is seen to include an internally-threaded inlet port 62, an internally-threaded outlet port 63, and an internally-threaded column connection port 64. The inlet and outlet ports 62 and 63 are conventionally configured chromatography ports used to couple interconnecting tubing to other chromatography equipment. The inlet and outlet ports 62 and 63 have an outer threaded section 65, an intermediate tapered or frusto-conical section 66, a small inner cylindrical section 67 terminating in a bottom shoulder face 68, and a small capillary flow path 69 communicating with the column connection port 64. Herein, the inlet port 62 is shown in-line with the column 10, and the outlet port 63 angled from a chamfered face of the adapter 60, but it should be readily apparent that other configurations and arrangements are possible.

The column connection port 64 is adapted to receive and hold the proximal end 70 of the chromatography column 10 when the protective end cap 14 is removed and the column 10 is threaded therein. The column connection port 64 has an outer internally-threaded section 71, a large intermediate cylindrical section 72, and a small inner cylindrical section 73 terminating in an inner shoulder face 74. The adapter 60 is attached to the column 10 by engaging the adapter internal threads 76 with the column external threads 25. When the column 10 is mounted, the extending sleeve 16 will be positioned in the connection port intermediate section 72 with its proximal end abutting the inner shoulder face 75. Similarly, the proximal end 47 of the extending capillary tube 17 will be positioned in the connection port inner section 73 abutting and sealingly engaging the shoulder face 74 with its upstream inlet 36 aligning and communicating with the opening to the flow path 69. An annular seal, or O-ring 77, is carried within a shell internal annular groove (not numbered) and provides a seal between the sleeve 16 and the adapter 17.

The adapter 60 includes a first fluid flow path 69 extending between the inlet port inner section 67 and the connection port inner section 73 to provide fluid communication with the inlet 36 of the capillary passage 35. The adapter 60 also includes a second fluid flow path 79 transverse to the first fluid flow path 69 extending angularly though the inner shoulder face 75 to provide a connection between the connection port intermediate section 72 and the inner section of the outlet port 63 enabling fluid communication with the proximal end filter 42 and thereby the proximal end of the column material 18.

In the embodiment shown in FIG. 7, the adapter 60 is seen to include a temperature control element 83, such as an electrical heating coil, which is disposed within a housing opening 84 adjacent the column connection port 64. A significant amount of chromatography is performed at controlled temperatures. The control element 83 provides a means for balancing or adjusting the temperature of fluids moving through the column 10 and block adapter 60 as needed. The short flow paths and counterflow-type column construction minimize temperature differences and gradients in the system. Creating short flow paths makes the chromatography analysis more efficient, because it provides low peak dispersion.

Figure 8:
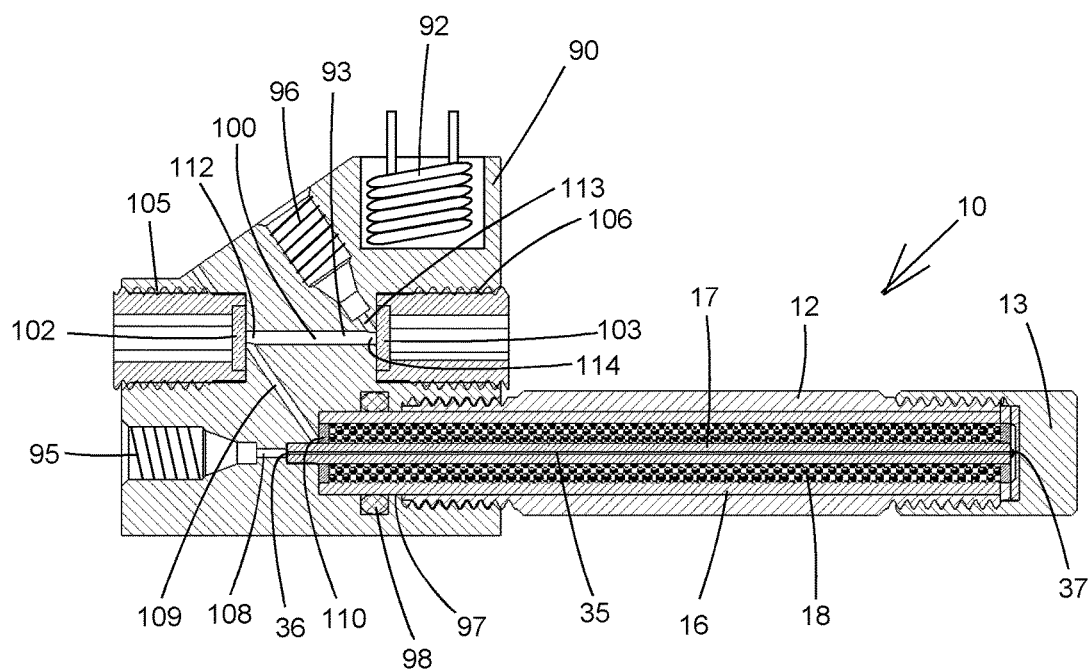
FIG. 8 is a cross-sectional view of the chromatography column shown in FIG. 4 attached to an adapter providing a flow cell for an optical detector.

In FIG. 8, another embodiment of the coupling adapter 90 is shown and includes a temperature control element 92 and an optical flow cell 93. Similar to adapter 60, the adapter 90 includes inlet and outlet ports 95 and 96, respectively, and column connection port 97 with sealing O-ring 98. The flow cell 93 is formed internally of the adapter 90 with an optical path 100 positioned between the column connection port 97 and the adapter outlet port 96. The flow cell 93 includes a pair of optical windows 102 and 103 mounted in a pair of threaded apertures 105 and 106, respectively, in spaced relation with the optical path 100 extending therebetween.

A first flow path 108 extends from the inlet port 95 downstream to the column connection port 97 to provide communication with connected capillary inlet 36. A second flow path 109 extends angularly from the downstream end 110 of the column 10 to the upstream end 112 of the optical path 100. A third flow path 113 extends angularly from the downstream end 114 of the optical path 100 downstream to the adapter outlet port 96. Herein, the various fluid paths are formed by boring into the adapter block from the exterior and then closing or blocking the bores by attaching the various components so that fluid flows in the desired directions.

It is understood that while the column and adapter described herein may replace currently used installation components, the other existing components need not be changed to accommodate their use.

Figure 9:
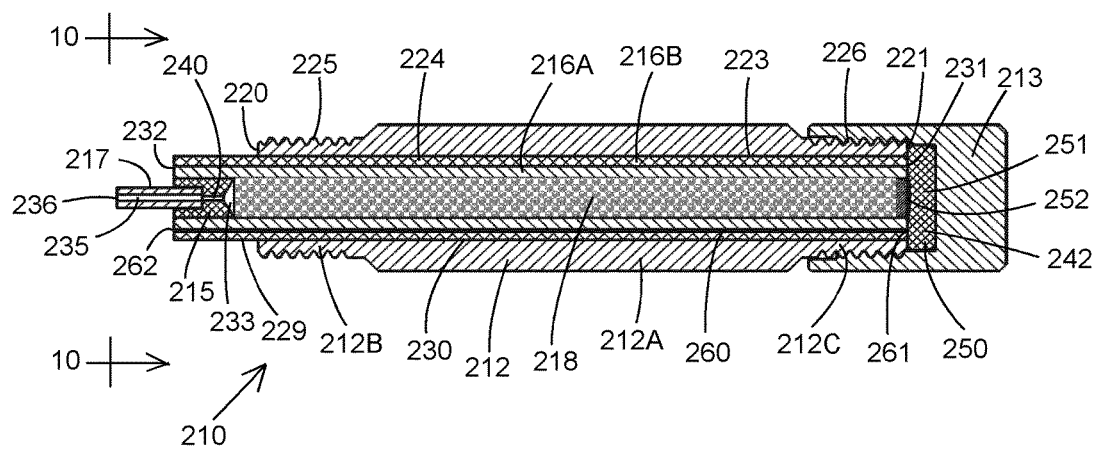
FIG. 9 is a cross-sectional view of a second embodiment of a chromatography column employing the principles of the invention; and, FIG. 10 is an end view and a partial enlargement of the chromatography column taken along line 10-10 of FIG. 9.
Figure 10:
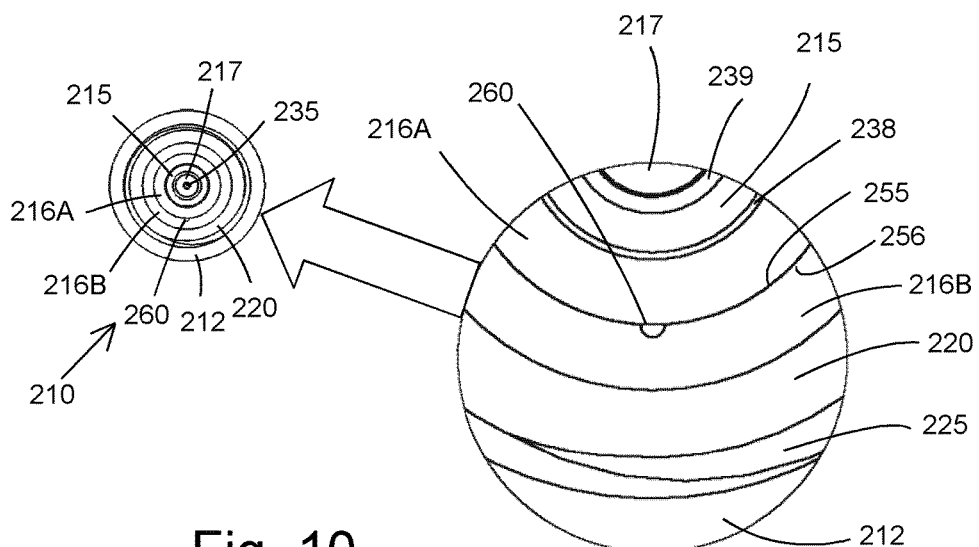

In FIGS. 9 and 10, another embodiment of a liquid chromatography column, generally designated 210, is shown and is seen to include an outer shell 212, an end cap 213, an end plug element 215, an inner sleeve 216A, an outer sleeve 216B, a capillary tube 217, and column material 218.

The elongate shell 212, or housing, extends along a longitudinal axis between proximal and distal ends 220 and 221, respectively, and has a cylindrical through bore 223 with an internal surface 230 defining an interior space 224. The shell 212 has an intermediate body section 212A extending between end sections 212B and 212C, each having external threads 225 and 226, respectively, adjacent ends 220 and 221. The end sections 212B and 212C are thereby adapted to be threaded into end caps or a coupling adapter as disclosed above. The shell 212 and end cap 213 can be made from any metal including stainless steel, but as contemplated herein can be inexpensively and easily produced from aluminum.

The cylindrical tubular sleeves 216A and 218B are concentric with the outer shell 212, the sleeve 216B having an external surface adjoining the shell internal surface 230. The coaxial sleeves 216A and 2216B have respective adjoining external surface 255 and internal surface 256 and are of a size and configuration to fit snugly with the shell 212 and with one another. A flow path is defined by a groove 260 formed in the internal surface of the outer sleeve 216B and closed by the external surface of the inner sleeve 216A. The groove 260 extends the length of the sleeves. The sleeves 216A and 216B have a distal end 231 aligned with the shell distal end 221 and a proximal end 232 extending axially outward from the shell proximal end 220. The internal surface of the inner sleeve 216A defines an interior space 233 that contains the column material 218.

To withstand high pressure, the inner sleeve 216A is made of stainless steel. The outer sleeve can be made from plastic, particularly from plastic materials that are generally non-reactive or chemically inert, including polyethylene, or from polytetrafluoroethylene ("Teflon®").

The end plug 215 is screwed into the upstream proximal end of the inner sleeve 216A by engagement of mating threads 238. The capillary tube 217 extends axially outward from the sleeve proximal end 232 and axially inward into a plug end opening (not numbered) engaging an internal shoulder formed at the opening bottom. The capillary tube 217 has a chamfer 239 along its outer proximal rim as seen in FIG. 10 to facilitate insertion into the coupling adapter. A flow passage 240 extends from plug opening to the sleeve interior space 233. At the downstream distal end of the inner sleeve 216A, an end element comprising a porous sintered metal filter 242, or frit, is located at the downstream distal end of the inner sleeve 216A. The column material 218 is thereby held between the plug 215 and the filter 242 within the enclosed interior space 233.

At the distal end of the shell 212 is a liquid spreader 250 comprising a stainless steel disk 251 having an inwardly-facing shallow cavity 252. The disk 251 closes the shell end and is held in place by the end cap 213 to seal the distal end of the shell 212 while allowing internal fluid flow from the sleeve interior space 233 outward to the upstream end of the sleeve groove 260.

In the previously disclosed embodiment, high pressure fluid entering the capillary proximal end is delivered to the distal end of the column material and flows toward the proximal end. In contrast, in this latter embodiment, high pressure fluid is delivered at the upstream proximal end of the column material, flows out of the downstream end of the column material, and then returns through the groove 260 and exist at an outlet at the column proximal end. As best seen in FIG. 9, fluid directed into the proximal end opening 236 of the capillary tube 217, flows from the capillary tube 217, through the plug into the upstream end of the column material 218, through the column material 218, downstream end filter 242 and spreader cavity 252, into the upstream groove inlet 261, and exits at the groove outlet 262, which is radially outward of the centrally disposed capillary tube.

INDUSTRIAL APPLICABILITY

It should be apparent the column and adapter described herein is a simple, functional unit that is effective and inexpensively manufactured.

The column design disclosed herein has an aluminum shell that transfers heat efficiently and uniformly.

The chromatography column described herein can be simply installed and removed without tools or fittings and provides a secure connection at any pressure. If a high pressure seal fails, the liquid flow will be directed to a detector and to a waste collector without creating external spillage. Further, the column performs more efficiently with close to zero dead volume geometry.

The use of aluminum permits the external shell to be anodized any color for purposes of coding or typing. There is sufficient space for labels, bar coding, and other identifying indicia.

Other aspects, objects and advantages of this invention can be obtained from a study of the drawings and the foregoing disclosure.

It should be understood that the terms "top," "bottom," "forward," "rearward," "first," "second," "upper," "lower," "inner," "outer," "inward," "outward," "proximal," "distal," "end," "side," "horizontal," "vertical," "height," "width," "length," and similar terms as used herein, have reference only to the structure shown in the drawings and are utilized only to facilitate describing the invention. The terms and expressions employed herein have been used as terms of description and not of limitation.

As used herein, the term "adjoin" shall mean "to be close to or in contact with"; the term "within" shall mean "to be partially or completely inside of"; the term "axial" refers to a longitudinal direction substantially parallel to the direction of column length; the term "transverse" refers to a direction other than the axial direction (e.g., orthogonal or nonorthogonal); the term "proximal" refers to an element normally oriented or positioned toward the column open end; the term "distal" refers to an element that is opposite the proximal end; and, the term "fluid" refers to both liquids and gases.

From the foregoing, it will be observed that numerous variations and modifications may be effected without departing from the spirit and scope of the invention. It will also be observed that the various elements of the invention may be in any number of combinations, and that all of the combinations are not enumerated here. It will be understood that no limitation with respect to the specific apparatus illustrated herein is intended or should be inferred. While specific embodiments of the invention have been disclosed, one of ordinary skill in the art will recognize that one can modify the materials, dimensions and particulars of the embodiments without straying from the inventive concept.

What is claimed is:

1. A chromatography column, comprising:
    a tubular shell with an open proximal end and a closed distal end and having a side wall with proximal and distal ends and an internal surface defining a first interior space;
    a tubular sleeve within said first interior space having a side wall with an external surface adjoining said internal surface of said shell, said sleeve having proximal and distal ends and an internal surface defining a second interior space;
    a porous end element at one end of said sleeve and a second end element at the other end of said sleeve closing the ends of the second interior space;
    column material within the second interior space between said end elements for separation of fluid flowing from an upstream end to a downstream end;
    a capillary tube extending axially outward from and axially into the proximal end of said sleeve, said capillary tube having at its proximal end an open upstream inlet and having at its distal end a downstream outlet in fluid communication with the upstream end of said column material;
    said sleeve defining a flow path extending downstream from the downstream end of said column material and having an outlet open to the exterior at the proximal end of said sleeve radially outward from said capillary tube; and,
    whereby fluid delivered into said capillary tube inlet at its proximal end flows through said column material and exits from the proximal end of said sleeve.

2. The chromatography column of claim 1 wherein said porous end element is at the proximal end of said sleeve, said second end element is porous and is at the distal end of said sleeve defining an end space with the closed distal end of the shell, and said capillary tube extends through both of said end elements with its outlet opening into the end space.

3. The chromatography column of claim 2 further including a spreader within the end space outward of said capillary tube outlet defining at least one flow path between said capillary tube outlet and said second end element.

4. The chromatography column of claim 1 wherein said shell is made from metal and said sleeve is made from chemically inert plastic.

5. The chromatography column of claim 1 wherein said porous end element is at the distal end of said sleeve, said second end element is at the proximal end of said sleeve and has an opening receiving the distal end of said capillary tube and a flow passage providing fluid communication between the capillary tube outlet and the upstream end of said column material, and further including a flow path defined by said sleeve providing fluid communication from the downstream end of said column material to an outlet at the proximal end of said sleeve radially outward from said capillary tube.

6. The chromatography column of claim 5 wherein said sleeve is comprised of an inner sleeve and an adjoining concentric outer sleeve, the internal surface of the outer sleeve defining a longitudinal groove closed by the external surface of the inner sleeve.

7. The chromatography column of claim 6 wherein said shell is made from metal, said inner sleeve is made from stainless steel, and said outer sleeve is made from chemically inert plastic.

8. The chromatography column of claim 1 wherein said sleeve extends outward from said proximal end of said shell.

9. The combination of the chromatography column set forth in claim 1 and a coupling adapter, said adapter comprising a column connection port adapted for receiving and holding said column, a fluid inlet port, a fluid outlet port, said adapter defining a first fluid passage extending between said inlet port upstream and said capillary tube inlet of a received column downstream and a second fluid passage extending from said proximal end of said sleeve of a received column upstream and communicating with said outlet port downstream, whereby fluid delivered upstream into said fluid inlet port, passes through the column, and exits downstream from said fluid outlet port.

10. The combination of claim 9 wherein said column connection port includes an inner cylindrical section having a first shoulder face defining a shoulder opening to a first flow path, an outer section with an internal thread, and an intermediate cylindrical section between said inner cylindrical section and said outer section defining a second shoulder face with a first opening for said capillary tube and a second opening to a second flow path, wherein said capillary tube extends into said inner cylindrical section and abuts said first shoulder face with said capillary tube inlet aligned with said shoulder opening, said sleeve extends into said intermediate cylindrical section and abuts said second shoulder face, and said shell has an external thread adjacent its proximal end adapted to engage said internal thread.

11. The combination of claim 10 further including an annular seal positioned between said sleeve and said intermediate cylindrical section.

12. The combination of claim 9 further including a temperature control element within said housing for adjusting the temperature of fluid passing through the adapter.

13. The combination of claim 9 further including an internal optical path intermediate the column connection port and fluid outlet port, said optical path having upstream and downstream ends, an optical window at each end of said optical path, said second flow path communicating with said upstream end of said optical path, and a third flow path between said downstream end of said optical path and said fluid outlet port.

14. The combination of claim 9 wherein said column connection port has an internal thread and said shell of said column has a complementary external thread to engage said internal thread and secure the column to said coupling adapter.

15. The chromatography column of claim 1 wherein said shell has an external thread adjacent its proximal end and further including a cap with a opening adapted to receive the proximal end of said shell, said shell cap a complementary internal thread adapted to engage said external thread and close the proximal end of said shell enclosing said sleeve and capillary tube.

16. The chromatography column of claim 1 wherein said shell includes a removable end cap for closing its distal end.

17. A chromatography column, comprising:
a tubular shell with an open proximal end and a closed distal end and having a side wall with proximal and distal ends and an internal surface defining a first interior space;
a tubular sleeve within the first interior space having a side wall with an external surface adjoining said internal surface of said shell, said sleeve having proximal and distal ends and an internal surface defining a second interior space;
a proximal porous element at the proximal end of said sleeve and a distal porous element at the distal end of said sleeve closing the ends of the second interior space and defining an end space with said closed distal end;
column material within the second interior space between said end elements for chromatographic separation of fluid flowing from a distal end to a proximal end;
a capillary tube extending axially outward from and into the proximal end of said sleeve, said capillary tube having at its proximal end an open upstream inlet and having at its distal end a downstream outlet within the end space; and,
whereby fluid delivered into said capillary tube inlet at its proximal end flows through said column material and exits from the proximal end of said sleeve.

18. The combination of the chromatography column set forth in claim 17 and a coupling adapter, said adapter comprising a column connection port adapted for receiving and holding said column, a fluid inlet port, a fluid outlet port, said adapter defining a first fluid passage extending between said inlet port upstream and said capillary tube inlet of a received column downstream and a second fluid passage extending from said proximal end of said sleeve of a received column upstream and communicating with said outlet port downstream, whereby fluid delivered upstream into said fluid inlet port, passes through the column, and exits downstream from said fluid outlet port.

19. A chromatography column, comprising:
a tubular shell with an open proximal end and a closed distal end and having a side wall with proximal and distal ends and an internal surface defining a first interior space;
a tubular sleeve within said first internal chamber having a side wall with an external surface adjoining said internal surface of said shell, said sleeve having proximal and distal ends and an internal surface defining a second interior space;
a porous end element at one end of said sleeve and a second end element at the other end of said sleeve closing the ends of the second interior space;
column material within the second interior space between said end elements for separation of fluid flowing from a proximal end to a distal end;
a capillary tube extending axially outward from and into the proximal end of said sleeve, said capillary tube having at its proximal end an open upstream inlet and having at its distal end a downstream outlet in fluid communication with the proximal end of said column material; and,
whereby fluid delivered into said capillary tube inlet at its proximal end flows through said column material and exits from the proximal end of said sleeve.

20. The combination of the chromatography column set forth in claim 19 and a coupling adapter, said adapter comprising a column connection port adapted for receiving and holding said column, a fluid inlet port, a fluid outlet port, said adapter defining a first fluid passage extending between said inlet port upstream and said capillary tube inlet of a received column downstream and a second fluid passage extending from said proximal end of said sleeve of a received column upstream and communicating with said outlet port downstream, whereby fluid delivered upstream into said fluid inlet port, passes through the column, and exits downstream from said fluid outlet port.

21. A chromatography column, comprising:
- a tubular shell with an open proximal end and a closed distal end and having a side wall with proximal and distal ends and an internal surface defining an internal chamber;
- a proximal porous element at the proximal end of said shell and a distal porous element adjacent the distal end of said shell defining an end space with said closed distal end;
- column material within the second interior space between said end elements for separation of fluid flowing from a proximal end to a distal end;
- a capillary tube having at its proximal end an open upstream inlet and having at its distal end a downstream outlet opening into the end space; and,
- whereby fluid delivered into said capillary tube inlet at its proximal end flows through said column material and exits the proximal end of said shell.

* * * * *